US012564565B2

(12) United States Patent
Fossati et al.

(10) Patent No.: US 12,564,565 B2
(45) Date of Patent: Mar. 3, 2026

(54) STABLE PHARMACEUTICAL FORMULATIONS OF AMINO ACIDS, PEPTIDES OR PROTEINS

(71) Applicant: IBSA Institut Biochimique SA, Lugano (CH)

(72) Inventors: Tiziano Fossati, Lugano (CH); Alessandro Di Maria, Lugano (CH)

(73) Assignee: IBSA Institut Biochimique SA, Lugano (CH)

( * ) Notice: Subject to any disclaimer, the term of this patent is extended or adjusted under 35 U.S.C. 154(b) by 0 days.

(21) Appl. No.: 19/209,056

(22) Filed: May 15, 2025

(65) Prior Publication Data

US 2025/0381159 A1     Dec. 18, 2025

Related U.S. Application Data

(63) Continuation of application No. PCT/IB2024/059401, filed on Sep. 26, 2024.

(30) Foreign Application Priority Data

Sep. 29, 2023    (IT) ........................ 102023000020130

(51) Int. Cl.
    *A61K 31/198*      (2006.01)
    *A61K 47/10*      (2017.01)

(52) U.S. Cl.
    CPC ............ *A61K 31/198* (2013.01); *A61K 47/10* (2013.01)

(58) Field of Classification Search
    CPC ......... A61K 31/198; A61K 47/10; A61K 9/08
    See application file for complete search history.

(56) References Cited

U.S. PATENT DOCUMENTS

| | | | |
|---|---|---|---|
| 3,035,974 | A | 5/1962 | Murray |
| 3,128,920 | A | 4/1964 | Volckening et al. |
| 5,951,989 | A | 9/1999 | Heymann |
| 6,458,842 | B1 | 10/2002 | Dickinson et al. |
| 7,723,390 | B2 | 5/2010 | Garavani et al. |
| 9,345,772 | B1 | 5/2016 | Parikh et al. |
| 11,096,913 | B2 | 8/2021 | Fossati et al. |
| 2003/0050344 | A1 | 3/2003 | Garavani et al. |
| 2003/0207802 | A1 | 11/2003 | DeFelippis et al. |
| 2004/0266877 | A1 | 12/2004 | Dickinson et al. |
| 2005/0059574 | A1 | 3/2005 | Klein et al. |
| 2010/0197790 | A1 | 8/2010 | Zoppetti et al. |
| 2014/0073695 | A1 | 3/2014 | Psarrakis et al. |
| 2014/0179785 | A1 | 6/2014 | Bellorini et al. |
| 2018/0353432 | A1 | 12/2018 | Carucci et al. |

FOREIGN PATENT DOCUMENTS

| | | |
|---|---|---|
| WO | WO 01/43762 A2 | 6/2001 |
| WO | WO 2010/057624 A1 | 5/2010 |

OTHER PUBLICATIONS

Ardi, M.S. et al., "Progress, prospect and challenges in glycerol purification process: A review," Renewable and Sustainable Energy Reviews, vol. 42, Nov. 18, 2014, pp. 1164-1173.
Austin, J. "Analysis of Drug Stability and Degradation," Pharm Anal Acta., vol. 13, Iss. 4, No. 1000667, May 6, 2022, pp. 1-2.
Felipe Laurie, V. et al., "Oxidation of Glycerol in the Presence of Hydrogen Peroxide and Iron in Model Solutions and Wine. Potential Effects on Wine Color," Journal of Agricultural and Food Chemistry, vol. 54, Iss. 13, May 25, 2006, pp. 4668-4673.
Lopes, A.P. et al., "Purified glycerol is produced from the frying oil transesterification by combining a pre-purification strategy performed with condensed tannin polymer derivative followed by ionic exchange," Fuel Processing Technology, vol. 187, May 2019, pp. 73-83.
PCT International Search Report and Written Opinion, PCT Application No. PCT/IB2024/059401, Feb. 24, 2025, 11 pages.
Rowe, R.C. et al., "Glycerin," Handbook of Pharmaceutical Excipients, 5th Edition, London: Pharmaceutical Press, GB, Jan. 1, 2006, pp. 301-303.
Swain, S. et al., "Stabilization and Delivery Approaches for Protein and Peptide Pharmaceuticals: An Extensive Review of Patents," Bentham Science, Recent Patents on Biotechnology, vol. 7, Iss. 1, Feb. 2013, pp. 28-46.

*Primary Examiner* — Snigdha Maewall
(74) *Attorney, Agent, or Firm* — FENWICK & WEST LLP

(57) ABSTRACT

The present disclosure relates to pharmaceutical formulations comprising an active ingredient belonging to the amino acid, peptide or protein classes and glycerin as excipient, characterized in that the glycerin has an iron content ≤0.2 ppm and an aldehyde and/or ketone species content ≤5 ppm.

11 Claims, No Drawings

STABLE PHARMACEUTICAL FORMULATIONS OF AMINO ACIDS, PEPTIDES OR PROTEINS

The invention relates to pharmaceutical formulations comprising an active ingredient belonging to the amino acid, peptide or protein classes and glycerin as excipient, characterised in that the glycerin has an iron content ≤0.2 ppm and an aldehyde and/or ketone species content ≤5 ppm.

PRIOR ART

Glycerin is often used as an excipient in a variety of formulations for oral, parenteral, topical and ophthalmic use. In said context, the word "excipient" denotes a substance used to dilute or carry the active ingredient of a medicament or a cosmetic so that it is easy to administer or apply.

Glycerin, which is mainly used as a solvent in oral and parenteral formulations, can be of synthetic or plant origin. Synthetic glycerin derives from olefins extracted from oil, whereas vegetable glycerin is a by-product of biodiesel which, in turn, derives from transesterification of vegetable fatty acids, such as rapeseed oil.

As vegetable glycerin has various origins, it naturally contains more impurities than synthetic glycerin. Various methods can be used to purify glycerin, such as distillation, acid treatments, and separation by passing through chelating resins or ion-exchange resins (M. S. Ardi et al., Renewable and Sustainable Energy Reviews; 42, 2015, 1164-1173).

It is known from the literature that the presence of metals catalyses oxidative degradation reactions (Austin J (2022). Analysis of Drug Stability and Degradation. Pharm Anal Acta. 13:667).

It is also known that amino acid structures and their sequences can degrade, giving rise to oxidative impurities. Said problem has proved particularly significant in the case of levothyroxine (T4), a hormone with an amino acid structure that tends to degrade with an oxidative path (Volker Neu et al. Anal Chem. 2013 Mar. 19; 85 (6)). However, the problem is also common with other medicaments having an amino acid structure, whether in monomeric or multimeric form, as in the case of peptides or proteins. Examples of widely used medicaments with an amino acid structure include levodopa, N-acetylcysteine, ademetionine, carnitine and acylated derivatives thereof, carnosine (a dipeptide obtained from the condensation reaction between β-alanine and L-histidine), essential and branched amino acids, and other compounds wherein amino acid functions are present. The class of medicaments comprising natural, synthetic or recombinant peptides or proteins, including vaccines, is even larger.

WO01/43762 discloses parenteral solutions comprising polypeptides and glycerin of non-animal origin comprising aldehyde species in amounts lower than 33 ppm. However, controlling the content of said aldehyde species in glycerin is not sufficient in itself to guarantee adequate stability of the amino acid compositions.

It is therefore crucial to ensure the stability of said active ingredients, by preventing degradation thereof caused by undesirable interactions with the excipients.

DESCRIPTION OF THE INVENTION

It has now been found that profiling the impurities in glycerin of any origin is crucial to ensure the stability of formulations of active ingredients with an amino acid, peptide or protein structure wherein glycerin is used as an excipient, in particular as a solvent or co-solvent.

In-depth studies conducted by the Applicant have identified the iron content of glycerin as a critical parameter to ensure the stability of levothyroxine (T4) and triiodothyronine (T3) formulations.

The ketone or aldehyde species, which are the oxidation products of glycerin have also proved to adversely affect the stability of T4. The degradation mechanisms activated by the iron ions and oxidised species present in glycerin are independent of the specific amino acid in question, whether in monomeric or multimeric form. The findings obtained with T4 can therefore be deemed to apply to active ingredients with an amino acid, peptide or protein structure in general.

In particular, it has been found that glycerin should have an iron content ≤0.2 ppm and an aldehyde and/or ketone species content ≤5 ppm in order to guarantee the stability of amino acids, peptides or protein. Contrary to the statements made in WO01/43762, it has been found that satisfactory stability can only be guaranteed by using glycerin with both an iron content ≤0.2 ppm and an aldehyde and/or ketone species content ≤5 ppm, as a low content of the latter is insufficient to ensure stability unless it is associated with an iron content ≤0.2 ppm, as will be demonstrated below.

A first object of the present invention therefore consists of pharmaceutical compositions comprising an active ingredient belonging to the amino acid, peptide or protein classes and glycerin as excipient, characterised in that the glycerin has an iron content ≤0.2 ppm and an aldehyde and/or ketone species content ≤5 ppm.

A second object of the invention is the use of glycerin having an iron content ≤0.2 ppm and an aldehyde and/or ketone species content ≤5 ppm as solvent or co-solvent for the preparation of stable liquid pharmaceutical compositions of amino acids, peptides or proteins.

A third object of the invention is a process for the preparation of pharmaceutical compositions comprising an active ingredient belonging to the amino acid, peptide or protein classes and glycerin as excipient, said process being characterised by a quantitation step of the iron content and aldehyde and/or ketone species content in the glycerin.

The compositions according to the invention can be in the form of oral solutions, soft capsules or oral films comprising a solution or dispersion in glycerin or glycerin-water mixtures. The invention also includes other types of formulation, such as parenteral or topical formulations.

The glycerin can be of vegetable, animal or synthetic origin. However, vegetable glycerin, which is less expensive than synthetic glycerin, is preferred.

The iron content and the aldehyde and/or ketone species content present in the glycerin can be quantitated with known, conventional analysis methods such as atomic absorption spectroscopy for the iron content and the dinitrophenylhydrazine assay for aldehyde and/or ketone species.

Batches of glycerin which fail to meet the specifications indicated should be rejected and optionally purified by conventional methods such as distillation, resin treatment and the like, until the desired purity is reached. The formulations according to the invention are also prepared with conventional pharmaceutical technologies, once the purity characteristics described herein have been established.

The invention is illustrated in greater detail in the following experimental part.

Various solutions of T4 in glycerin were prepared at the concentration of 100 μg/mL, using glycerins from different suppliers which had undergone different purification processes.

The resulting solutions of T4 in glycerin were subjected to analysis of the metals and reactive aldehyde and ketone species originating from oxidative processes.

The aldehyde and ketone species content present was determined with methods already known in the literature (e.g. V. Felipe Laurie et al., J. Agric. Food Chem. 2006, 54, 4668-4673), which involve reacting said species with DNPH (2,4-dinitrophenylhydrazine) followed by chromatographic analysis.

The solutions underwent forced degradation at 50° C. for 28 days. The T4 content was analysed at time zero and after 28 days, and its reduction was calculated as a percentage of its initial value.

Table 1 shows the results obtained for each batch analysed.

TABLE 1

| Batch | Formulation | Fe ppm | Aldehyde and/or ketone species (DNPH assay ) ppm* | Reduction of % T4 after 28 days at 50° C. |
|---|---|---|---|---|
| 1 | Vegetable glycerin | 0.23 | 24.5 | −14.6 |
| 2 | Purified vegetable glycerin a | 0.06 | 27.7 | −8.3 |
| 3 | Synthetic glycerin | 0.12 | 1.8 | −5 |
| 4 | Purified vegetable glycerin b | 0.13 | 0.3 | −1 |
| 5 | Vegetable glycerin | 0.07 | 21.3 | −9 |
| 6 | Vegetable glycerin | 0.06 | 9.4 | −9 |

*Expressed as ppm of formaldehyde

The results demonstrate that amounts of Fe $\leq 0.2$ ppm and values of DNPH-reactive aldehyde and/or ketone species $\leq 5$ ppm guarantee that the reduction in content of T4 solubilised in glycerin under forced degradation conditions (28 days at 50° C.) is $\leq 5\%$.

Table 2 shows the results of a similar experiment to the one reported above, but using a glycerin with a higher iron content than that claimed, and an aldehyde and ketone content of less than 5 ppm

TABLE 2

| Type of glycerin | Fe (ppm) | Aldehyde and/or ketone species (DNPH assay) ppm* | T4 content at time zero | T4 content 28 days at 50° C. | AT4 (%) after 28 days at 50° C. after 28 days at 50° C. |
|---|---|---|---|---|---|
| purified vegetable glycerin | 0.42 | 0.5 | 101.2 | 89 | −12 |

*Expressed as formaldehyde content

The results prove that the use of a glycerin with a low aldehyde species content (e.g. amounting to 33 ppm as reported in WO 01/43762) is insufficient to stabilise the formulation. The iron content is also critical and should be less than or equal to 0.2 ppm.

The invention claimed is:

1. A stable pharmaceutical composition comprising:
an active ingredient that is L-thyroxine (T4); and
glycerin having:
    $\leq 0.2$ ppm iron, and
    $\leq 5$ ppm aldehyde and/or ketone species;
wherein the glycerin is of vegetable origin.

2. The pharmaceutical composition of claim 1, wherein the pharmaceutical composition further comprises water.

3. The pharmaceutical composition of claim 1, wherein the pharmaceutical composition is an oral solution.

4. The pharmaceutical composition of claim 3, wherein the glycerin is comprised in a glycerin-water mixture.

5. The pharmaceutical composition of claim 1, wherein the pharmaceutical composition is in form of a soft capsule.

6. The pharmaceutical composition of claim 1, wherein the glycerin is comprised in a glycerin-water mixture.

7. The pharmaceutical composition of claim 1, wherein the aldehyde and/or ketone species is 2,4-dinitrophenylhydrazine (DNPH)-reactive.

8. A process for the preparation of a stable pharmaceutical composition, the process comprising:

combining an active ingredient that is L-thyroxine (T4)
    with glycerin having:
    $\leq 0.2$ ppm iron, and
    $\leq 5$ ppm aldehyde and/or ketone species,
    wherein the glycerin is of vegetable origin.

9. The process of claim 8, wherein the glycerin is comprised in a glycerin-water mixture.

10. The process of claim 8, further comprising quantitating the iron content in the glycerin to determine whether the iron content is $\leq 0.2$ ppm.

11. The process of claim 8, further comprising quantitating the aldehyde and/or ketone species content in the glycerin to determine whether the aldehyde and/or ketone species content is $\leq 5$ ppm.

* * * * *